United States Patent [19]

Cordier et al.

[11] Patent Number: 4,532,350

[45] Date of Patent: Jul. 30, 1985

[54] PROCESS FOR THE SELECTIVE PREPARATION OF META-CHLOROANILINES

[75] Inventors: Georges Cordier, Francheville; Pierre Fouilloux, Caluire, both of France

[73] Assignee: Rhone-Poulenc Agrochimie, Lyons, France

[21] Appl. No.: 454,887

[22] Filed: Dec. 30, 1982

Related U.S. Application Data

[63] Continuation of Ser. No. 283,153, Jul. 14, 1981, abandoned.

[30] Foreign Application Priority Data

Aug. 1, 1980 [FR] France .................................. 80 17325

[51] Int. Cl.$^3$ .............................................. C07C 85/24
[52] U.S. Cl. ..................................... 564/412; 564/305; 564/309; 564/315; 564/330; 564/417
[58] Field of Search ................ 564/305, 315, 412, 417

[56] References Cited

U.S. PATENT DOCUMENTS

| | | | |
|---|---|---|---|
| 3,888,929 | 6/1975 | Rivier | 564/412 |
| 4,085,141 | 4/1978 | Wedemeyer et al. | 564/315 X |
| 4,206,147 | 6/1980 | Daumas et al. | 564/412 |
| 4,206,148 | 6/1980 | Biola et al. | 564/412 |
| 4,340,759 | 7/1982 | Cordier | 564/412 |

*Primary Examiner*—Robert V. Hines
*Attorney, Agent, or Firm*—Browdy and Neimark

[57] ABSTRACT

Process for the selective preparation of metachloroanilines.

It is carried out by the hydrodechlorination of polychloroanilines or polychloronitrobenzenes with hydrogen, in the liquid phase and in an acid medium, under the action of heat and under pressure, in the presence of a noble metal used in association with a heavy metal.

These meta-chloroanilines are intermediates especially for active plant-protection substances.

20 Claims, No Drawings

PROCESS FOR THE SELECTIVE PREPARATION OF META-CHLOROANILINES

This is a continuation of application Ser. No. 283,153 filed July 14, 1981, now abandoned.

The present invention relates to a process for the preparation of anilines substituted by chlorine in the meta-position, by reacting hydrogen with nitrogen-containing aromatic compounds which are more highly halogen-substituted. Meta-chloroanilines are intermediates especially for the manufacture of active plant-protection substances.

The preparation of chloroanilines substituted in the meta-position by reacting polychloroanilines with hydrogen under pressure, in an acid medium, in the presence of a catalyst based on a noble metal, has been described in French Pat. No. 2,298,531 corresponding to U.S. Pat. No. 4,085,141. However, the process described requires the use of high pressures and very large amounts of hydrochloric acid, which presents serious corrosion problems.

French patent application No. 79/04,482, corresponding to U.S. application Ser. No. 115,137 and now U.S. Pat. No. 4,340,759, describes a process for the preparation of anilines substituted in the meta-position by chlorine, by hydrodechlorination in an acid medium, under particular conditions, the reaction being furthermore carried out in the presence of heavy metal cations in the aqueous medium. This makes it possible to carry out the reaction under more moderate temperature and pressure conditions.

It has now been discovered that it is possible, for this same purpose, to use the noble metal in association with a heavy metal, which will be defined below, as a solid catalyst, i.e. in solid metallic form.

More particularly, the present invention relates to a process for the preparation of anilines substituted in the meta-position by chlorine, by the catalytic hydrogenation, in the liquid phase, under the action of heat and under pressure, in the presence of noble metals from group VIII of the periodic classification, of nitrogen-containing and chlorine-containing benzene derivatives of the formula:

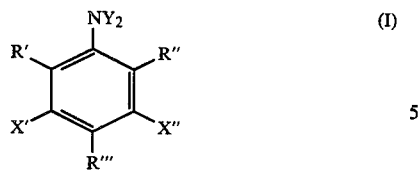

in which: Y represents the hydrogen atom or the oxygen atom, X' and X", which are identical to or different from one another, each represent a chlorine atom or an optionally substituted alkyl, aryl, aralkyl, alkoxy or aralkoxy radical, at least one of the symbols X' and X" necessarily being a chlorine atom and it furthermore being possible for one of the symbols X' and X" to be hydrogen, and R', R" and R"', which are identical to or different from one another, each represent a chlorine atom or an optionally substituted alkyl, aralkyl, alkoxy or aryloxy radical, at least one of these three symbols representing the chlorine atom and it being furthermore possible for at most two of the symbols R', R" or R"' to be hydrogen, in which process the reaction is carried out in the presence of a co-catalyst based on at least one heavy metal belonging to one of the groups Ib to Va of the periodic classification.

Suitable heavy metals which may be mentioned in particular are bismuth, lead, tin, thallium, mercury and silver. It has been found, in particular, that good results are obtained using silver.

As has been stated, the reaction is carried out in the liquid phase; in practice, it is advantageously carried out in the presence of an inorganic solvent which is liquid and inert under the operating conditions. The term "inert solvent" is to be understood as meaning a solvent which does not react chemically under the reaction conditions. In fact, it is preferred to use water.

The acidity of the reaction medium is generally such that the pH (in the case of an aqueous medium) is advantageously below 1.5, preferably below 1. The concentration of $H^+$ ions in the medium is generally between 0.5 and 12 gram ions/liter and preferably between 1 and 6 gram ions of $H^+$/liter. Higher concentrations of acid can be used, but to no great advantage.

The acidity of the reaction medium can be obtained by means of strong mineral acids such as sulphuric, phosphoric or hydrohalic acids, or strong organic acids; however, it is preferred to use hydrohalic acids and more especially hydrochloric acid. In any case, in view of the presence of chloride ions produced by the dehalogenation, the reaction is in fact carried out at least partially in the presence of hydrochloric acid.

The process according to the invention is carried out in the liquid phase (except, of course, for the catalyst based on a noble metal and a heavy metal). The liquid phase can be homogeneous and constitute a solution; this is a preferred embodiment, especially if Y is the oxygen atom in the formula (I); a liquid phase of this type thus contains the reactants, the reaction products and the solvent or solvents which may be present. It is also possible to carry out the reaction with two liquid phases.

The pressure at which the reaction is carried out is generally above 3 bars (relative pressure) and preferably above 5 bars. There is no critical upper limit to the pressure, but, for economic reasons, it is generally advantageous to carry out the reaction at pressures below 100 bars, pressures below 20 bars being preferred.

The reaction temperature is generally between 90° and 300° C., preferably between 110° and 200° C. In the case where relatively volatile acids are used, an elevated temperature can lead to the existence of a relatively high partial pressure for the compounds, other than hydrogen, in the vapour phase (the term "vapour phase" is obviously to be understood as meaning the vapour phase surmounting the liquid reaction medium). The operating conditions are generally chosen so that the partial pressure of hydrogen is between 10 and 80% of the total pressure (relative pressure) and preferably between 30 and 60%.

The noble metals forming the base of the catalysts used in the invention are mainly metals from group VIII of the periodic classification, such as ruthenium, rhodium, palladium, osmium, iridium and platinum; palladium is the preferred metal. The metal can be in the metallic form or in the form of a chemical compound; in general, the metal is preferably used in the metallic form because, under the operating conditions, the compounds tend to be reduced to the metallic form (oxidation state=zero).

The catalyst can be supported or unsupported. Any support which is in itself known for supporting catalysts can be used as the catalyst support, provided that this support is resistant to water and to acids; more particularly suitable supports which may be mentioned are carbon black, silica and barium sulphate; active charcoal is a preferred support. The catalyst and also its support are advantageously in a finely divided form; specific surface areas of more than 100 m$^2$/g are generally suitable.

The amount of catalyst used is such that the proportion by weight of noble metal of the catalyst, relative to the compound of the formula (I) to be treated, is generally between 0.01 and 10%, preferably between 0.1 and 5%.

The heavy metals used in association with the noble metal in the invention act in practice as a catalyst promoting the formation of meta-chloroamines. These heavy metals can be used in the metallic form or in the form of solid compounds. The metallic form is preferred because, under the operating conditions of a strongly reducing nature, the compounds tend to be reduced to the metallic form (oxidation state=zero). It has been found that good results are obtained with silver and tin. The amounts of heavy metal, relative to the catalyst based on a noble metal, and expressed as a molar ratio, are most frequently between 0.1 and 10 and preferably between ⅓ and 3. Higher ratios can be used, but the proportion of noble metal becomes low, the reaction becomes very slow and the process loses its economic value.

The following may preferably be mentioned as compounds of the formula (I) which are capable of being treated by the process of the invention: 2,3-dichloronitrobenzene and 2,3-dichloroaniline; 2,5-dichloronitrobenzene and 2,5-dichloroaniline; 3,4-dichloronitrobenzene and 3,4-dichloroaniline; 2,3,4-trichloronitrobenzene and 2,3,4-trichloroaniline; 2,3,5-trichloronitrobenzene and 2,3,5-trichloroaniline; 2,3,6-trichloronitrobenzene and 2,3,6-trichloroaniline; 2,4,5-trichloronitrobenzene and 2,4,5-trichloroaniline; 3,4,5-trichloronitrobenzene and 3,4,5-trichloroaniline; 2,3,4,6-tetrachloronitrobenzene and 2,3,4,6-tetrachloroaniline; 2,3,4,5-tetrachloronitrobenzene and 2,3,4,5-tetrachloroaniline; 2,3,5,6-tetrachloronitrobenzene and 2,3,5,6-tetrachloroaniline; and pentachloronitrobenzene and pentachloroaniline; the following may also be mentioned: 4,5,6-trichloro-2-methylnitrobenzene and 4,5,6-trichloro-2-methylaniline; 2,5-dichloro-4-methylnitrobenzene and 2,5-dichloro-4-methylaniline; 2,3,5,6-tetrachloro-4-methylnitrobenzene and 2,3,5,6-tetrachloro-4-methylaniline; 2,5-dichloro-3,4-dimethylnitrobenzene and 2,5-dichloro-3,4-dimethylaniline; 2,5-dichloro-4-ethylnitrobenzene and 2,5-dichloro-4-ethylaniline; 2,5-dichloro-4-propylnitrobenzene and 2,5-dichloro-4-propylaniline; 3,4,6-trichloro-2-benzylnitrobenzene and 3,4,6-trichloro-2-benzylaniline; 2,2'-dinitro-3,5,6,3',5',6'-hexachlorodiphenylmethane and 2,2'-diamino-3,5,6,3',5',6'-hexachlorodiphenylmethane; 2-nitro-3,4,5-trichlorobiphenyl and 2-amino-3,4,5-trichlorobiphenyl; 4,4'-dinitrooctachlorobiphenyl and 4,4'-diaminooctachlorobiphenyl; 4,5-dichloro-2-methoxynitrobenzene and 4,5-dichloro-2-methoxyaniline; 3,4-dichloro-2-methoxynitrobenzene and 3,4-dichloro-2-methoxyaniline; 3,6-dichloro-2-methoxynitrobenzene and 3,6-dichloro-2-methoxyaniline; 5,6-dichloro-2-methoxynitrobenzene and 5,6-dichloro-2-methoxyaniline; 3,4,6-trichloro-2-methoxynitrobenzene and 3,4,6-trichloro-2-methoxyaniline; 3,4,5-trichloro-2-methoxynitrobenzene and 3,4,5-trichloro-2-methoxyaniline; 3,4,5,6-tetrachloro-2-methoxynitrobenzene and 3,4,5,6-tetrachloro-2-methoxyaniline; 4,5-dichloro-3-methoxynitrobenzene and 4,5-dichloro-3-methoxyaniline; 5,6-dichloro-3-methoxynitrobenzene and 5,6-dichloro-3-methoxyaniline; 2,5-dichloro-3-methoxynitrobenzene and 2,5-dichloro-3-methoxyaniline; 4,5,6-trichloro-3-methoxynitrobenzene and 4,5,6-trichloro-3-methoxyaniline; 2,4,5,6-tetrachloro-3-methoxynitrobenzene and 2,4,5,6-tetrachloro-3-methoxyaniline; 2,3-dichloro-4-methoxynitrobenzene and 2,3-dichloro-4-methoxyaniline; 2,5-dichloro-4-methoxynitrobenzene and 2,5-dichloro-4-methoxyaniline; 2,3,6-trichloro-4-methoxynitrobenzene and 2,3,6-trichloro-4-methoxyaniline; 2,3,5-trichloro-4-methoxynitrobenzene and 2,3,5-trichloro-4-methoxyaniline; 2,3,5,6-tetrachloro-4-methoxynitrobenzene and 2,3,5,6-tetrachloro-4-methoxyaniline; 4,5-dichloro-2-phenoxynitrobenzene and 4,5-dichloro-2-phenoxyaniline; 3,4,5,6-tetrachloro-2-phenoxynitrobenzene and 3,4,5,6-tetrachloro-2-phenoxyaniline; 2,4,5,6-tetrachloro-3-phenoxynitrobenzene and 2,4,5,6-tetrachloro-3-phenoxyaniline; 2,5-dichloro-4-phenoxynitrobenzene and 2,5-dichloro-4-phenoxyaniline; and 2,3,5,6-tetrachloro-4-phenoxynitrobenzene and 2,3,5,6-tetrachloro-4-phenoxyaniline.

The following may preferably be mentioned amongst the anilines, substituted in the meta-position by a chlorine atom, which are capable of being prepared by the process according to the invention: meta-chloroaniline and 3,5-dichloroaniline; the following may also be mentioned: 5-chloro-2-methylaniline, 5-chloro-3-methylaniline, 3-chloro-4-methylaniline, 3,5-dichloro-4-methylaniline, 5-chloro-3,4-dimethylaniline, 3-chloro-4-ethylaniline, 3-chloro-2-benzylaniline, 4,4'-diamino-2,6,2',6'-tetrachlorobiphenyl, 3-chloro-2-methoxyaniline, 5-chloro-2-methoxyaniline, 3,5-dichloro-2-methoxyaniline, 3-chloro-4-methoxyaniline, 5-chloro-3-methoxyaniline, 3,5-dichloro-4-methoxyaniline, 3-chloro-2-phenoxyaniline, 5-chloro-2-phenoxyaniline, 3,5-dichloro-2-phenoxyaniline and 3,5-dichloro-4-phenoxyaniline.

The process according to the invention can be carried out continuously or batchwise. At the end of the reaction, the catalyst and the co-catalyst can be separated off, if appropriate, by filtration or by equivalent means such as centrifugation; the meta-chloroaniline prepared can be separated off by means which is in itself known, for example by means of solvent extraction and/or by distillation; before carrying out this separation, it is generally appropriate to reconvert the aniline (salified in the acid medium) into the amine form (unsalified) by neutralisation or alkalisation with the aid of an alkaline agent.

The process according to the invention is very advantageous because of its good selectivity with respect to meta-chloroamine and because of the relatively mild conditions which it makes it possible to use.

The examples, which are given without implying a limitation, illustrate the invention and show how it can be put into effect.

EXAMPLE 1

2,3,4,5-Tetrachloroaniline (0.42 g), a catalyst consisting of palladium and silver deposited on active charcoal (specific surface area of the active charcoal: 1,100 m$^2$/g; proportion by weight of palladium: 3%; proportion by weight of silver: 2%) (0.07 g) and an aqueous solution of hydrochloric acid having a concentration of 4 mols/ liter (120 cc) are introduced into a 250 cc tantalum-lined autoclave.

The autoclave is closed and purged first with argon and then with hydrogen. It is then heated to 160° C. whilst allowing the autogenous pressure to increase, and then, when this temperature has been reached, hydrogen is introduced up to a total (relative) pressure of 13 bars, the partial pressure of hydrogen being 6 bars.

The reaction is allowed to proceed under these conditions for 2 hours. The autoclave is cooled; the liquid reaction mixture is rendered alkaline with an aqueous solution of sodium hydroxide (NaOH); the catalyst is filtered off; 3,5-dichloroaniline is extracted from the aqueous phase with methylene chloride; the methylene chloride solution thus obtained is dried over sodium sulphate; the solvent is evaporated off in vacuo.

The degree of conversion of the tetrachloroaniline was 100%. The yield of 3,5-dichloroaniline obtained is 98%. The proportion of silver in the medium is 0.00006 gram ion/liter.

EXAMPLE 2

The reaction is carried out as in Example 1, the catalyst being replaced by a catalyst consisting of palladium (proportion by weight: 4%) and silver (proportion by weight: 1%), the support being the same as previously. The reaction lasts 1 hour 10 minutes.

Under these conditions, 3,5-dichloroaniline is obtained with a yield of 87% and 3-chloroaniline is obtained as a by-product with a yield of 10%, the degree of conversion of the tetrachloroaniline being 100%.

We claim:

1. A process for the preparation of anilines substituted in the meta-position by chlorine, by the catalytic hydrogenation, in the liquid phase, under the action of heat and under pressure, in the presence of noble metals from group VIII of the periodic classification, of nitrogen-containing and chlorine-containing benzene derivatives of the formula:

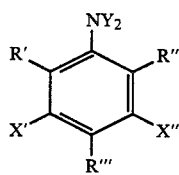

(I)

in which: Y represents the hydrogen atom or the oxygen atom, X' and X", which are identical to or different from one another, each represent a chlorine atom or an optionally substituted alkyl, aryl, aralkyl, alkoxy or aralkoxy radical, at least one of the symbols X' and X" necessarily being a chlorine atom and it furthermore being possible for one of the symbols X' and X" to be hydrogen, and R', R" and R'", which are identical to or different from one another, each represent a chlorine atom or an optionally substituted alkyl, aralkyl, alkoxy or aryloxy radical, at least one of these three symbols representing the chlorine atom and it being furthermore possible for at most two of the symbols R', R" or R'" to be hydrogen, in which process the reaction is carried out in the presence of a co-catalyst based on at least one heavy metal in solid metallic form belonging to one of the groups Ib to Va of the periodic classification.

2. A process according to claim 1, wherein the heavy metal is chosen from the group comprising bismuth, lead, tin, thallium, mercury and silver.

3. A process according to claim 1, wherein the heavy metal is silver.

4. A process according to claim 1, wherein the amounts of heavy metal, relative to the catalyst based on a noble metal, and expressed as a molar ratio, are between 0.1 and 10.

5. A process according to claim 1, wherein R', R", R'", X' and X", which are identical to or different from one another, represent the hydrogen atom or the chlorine atom.

6. A process for the preparation of optionally substituted meta-dichloroanilines, according to claim 1, wherein X' and X" represent the chlorine atom.

7. A process for the preparation of optionally substituted meta-monochloroanilines, according to claim 1, wherein only one of the two radicals X' X" is the chlorine atom.

8. A process for the preparation of 3,5-dichloroaniline, according to claim 1, wherein: Y is the hydrogen or oxygen atom, X' and X" are the chlorine atom and R', R" and R'" are the hydrogen atom or the chlorine atom, at least one of them being the chlorine atom.

9. A process according to claim 1, wherein the pH is less than 1.5.

10. A process according to claim 9, wherein the pH is less than 1.

11. A process according to claim 1, wherein the reaction medium is an aqueous medium.

12. A process according to claim 1, wherein the reaction medium only contains a liquid phase, except for the catalyst based on a noble metal and a heavy metal.

13. A process according to claim 1, wherein the total pressure is between 3 and 100 bars.

14. A process according to claim 13, wherein the total pressure is between 5 and 20 bars.

15. A process according to claim 1, wherein the temperature is between 90° and 300° C.

16. A process according to claim 1, wherein the partial pressure of hydrogen is between 10 and 80% of the total pressure.

17. A process according to claim 16, wherein the partial pressure of hydrogen is between 30 and 60% of the total pressure.

18. A process according to claim 1, wherein the noble catalyst is palladium.

19. A process according to claim 1, wherein the proportion by weight of noble metal, relative to the compound of the formula (I), is between 0.01 and 10%.

20. A process for the preparation of 3,5-dichloroaniline according to claim 1 wherein Y is hydrogen or oxygen, X' and X" are each chlorine, and R', R" and R'" are each hydrogen or chlorine with at least one of them being chlorine;
   the amount of heavy metal, relative to the noble metal catalyst, and expressed as a molar ratio, is between 0.1 to 10;
   the reaction medium, except for the catalyst based on a noble metal and the heavy metal, consists of an aqueous phase in which the pH is less than 1; and
   the total pressure is between 3 and 100 bars.

* * * * *